United States Patent [19]

Catone

[11] Patent Number: 5,373,860
[45] Date of Patent: Dec. 20, 1994

[54] APPARATUS FOR AND METHOD OF CONTOURING PLATES FOR BONE FIXATION

[76] Inventor: Guy A. Catone, 620 Amberson, Pittsburgh, Pa. 15232

[21] Appl. No.: 161,979

[22] Filed: Dec. 3, 1993

Related U.S. Application Data

[63] Continuation of Ser. No. 934,952, Aug. 25, 1992, abandoned.

[51] Int. Cl.$^5$ .............. A61B 19/00; A61F 2/02; A61F 2/28; A61F 2/54
[52] U.S. Cl. .................. 128/898; 128/897; 623/11; 623/16; 623/66; 623/901; 425/2; 264/222
[58] Field of Search .............. 128/897, 898; 623/11, 623/16, 18, 66, 901; 433/167, 171, 199.1, 200.1, 213, 214; 264/222, 320, 325; 425/2

[56] References Cited

U.S. PATENT DOCUMENTS

| | | | |
|---|---|---|---|
| 2,124,767 | 7/1938 | Dawn | 623/66 X |
| 4,693,721 | 9/1987 | Ducheyne | 623/66 X |
| 4,695,254 | 9/1987 | Herrell | 433/213 |
| 4,828,495 | 5/1989 | Bell et al. | 623/16 X |
| 4,920,580 | 5/1990 | Liff | 623/66 X |
| 4,995,812 | 2/1991 | Reynolds | 433/214 |
| 5,066,351 | 11/1991 | Knoll | 264/320 X |

Primary Examiner—Randall L. Green
Assistant Examiner—Dinh X. Nguyen
Attorney, Agent, or Firm—Reed Smith Shaw & McClay

[57] ABSTRACT

A method of contouring bone plates or other bone fixation element is set forth comprising the steps of making a molded impression of the surface of the area to which the bone plate is to be fixed, appropriately positioning the bone plate to be contoured relative to the molded impression of the molding material to contour the bone plate to the molded impression when sufficient compressive force is applied to the bone plate, and applying sufficient compressive force to the bone plate to contour the bone plate to the shape of the molded impression, thereby contouring the bone plate to the surface of the fixation area. An apparatus for contouring bone plates with substantial accuracy is also set forth comprising a means for forming a molded impression of the surface of the area to which the bone plate is to be fixed, a compression member, and a means for applying sufficient compressive force to the compression member to contour the bone plate to the molded impression of the mold forming means.

7 Claims, 10 Drawing Sheets

APPARATUS FOR AND METHOD OF CONTOURING PLATES FOR BONE FIXATION

This is a continuation of copending application Ser. No. 07/934,952 filed on Aug. 25, 1992 abandoned.

FIELD OF THE INVENTION

The present invention relates to a method and apparatus for fixation of bone plates, and, in particular, to a method and apparatus for contouring bone plates to the surface of the fixation area with substantial precision.

BACKGROUND OF THE INVENTION

The use of metal plates and screws to immobilize bone fragments dates back to the nineteenth century. Because of problems with infection and technical failures, however, the concept was not widely accepted. Bone plating for major long bones using the principle of axial compression was reintroduced with a great degree of success in the 1940s. I. R. Munroe, "The Luhr Fixation System For The Craniofacial Skeleton", 16 *Clinics In Plastic Surgery*, 41 (January 1989). Luhr and others started to use metal plates and screws in mandibular fractures in the late 1960s. Rigid fixation of facial skeletal fractures and osteotomies was started approximately a decade later, but was not widely accepted in North America. More recently, however, a rapid expansion of utilization of plates and screws for fractures, osteotomies and reconstruction of the entire craniofacial skeleton has occurred.

There are numerous bone plating systems on the market from a great number of orthopedic and maxillofacial companies throughout the world that enable surgical repair of facial bone fractures involving the frontal bones, the cranium, the orbital regions, the nose, the maxilla (upper jaw), and the mandible (lower jaw), etc. Many of these systems are constructed by laser cutting. The precision of compression and non-compression of bone plating systems is thus extraordinary.

Because of the influence of general orthopedics on facial bone surgery, early on, relatively large plates and screws were developed for rigid fixation of mandibular and maxillary fractures and osteotomies. Extremity > fractures involve strong bones that are exposed to remarkable muscle traction and compression forces and require larger plates that can withstand these forces until bone healing is complete. The very complex craniofacial skeleton, however, shows numerous areas of thin bones that are not exposed to any remarkable muscle actions and therefore do not need such strong and relatively large plates. This analysis has led to the development of "mini" or "micro" plates and screws of remarkably smaller dimension as compared to the plating systems used with bones of the extremities. Luhr, H. G., "Indications for Use of a Microsystem for Internal Fixation in Craniofacial Surgery," 1 The Journal of Craniofacial Surgery 35 (January 1990). Recently, mesh systems have also been developed for bridging bony defects.

One of the most commonly used plating system developed to date is the Luhr system manufactured by Howmedica, Inc. The use of mandibular compression screw plates for the repair of mandibular fractures was first published by Luhr in 1968. Luhr, H. G., "Zur Stabilen Osteosynthese Bei Unterkieferfrakturne", *Dtsh. Zahnarztl* Z 23:754 (1968). Subsequently, based on the original concept by Luhr, several complete systems have been developed for use in all the various situations encountered in trauma and reconstructive surgery of the facial skeleton.

These systems include (1) the mandibular compression-screw system ("MCS") for the treatment of mandibular fractures (particularly designed for the intraoral approach); (2) the mini-compression system for the treatment of mid-face fractures, for reconstructive surgery of the facial skeleton and the skull, and for orthognathic surgery; (3) the mandibular reconstruction system ("MRS") for the reconstruction of mandibular defects, including condyle replacement; and (4) the micro-Luhr system. Luhr, H. G., "Vitallium Luhr Systems For Reconstructive Surgery Of The Facial Skeleton", *The Otolaryngologic Clinics of North America*, 573 (August, 1987). Other systems include the Wurzberg system marketed by Walter Lorenz and a new system being developed by Micro-Aire.

The main characteristics of the Luhr systems are as follows:

1. The plates and screws consist of the cobalt chromium molybdenum alloy vitallium (Howmedica, Inc.). Vitallium combines the property of high resistance to corrosion with optimal mechanical strength.
2. The systems are designed to provide automatic axial compression to the fracture or osteotomy line (as well as to bone grafts). This is provided by means of eccentric plate holes and screws with conical screw heads. This automatic axial compression provides optimal reduction and maximum stability.
3. The systems employ self-tapping screws. These shorten the duration of surgery and provide firm anchorage of the screws even in small bones.
4. Each of the systems consists of specially designed implants and instruments for that system. These are clearly arranged in sterilized boxes. The various implants have been designed to meet the needs of the maxillofacial surgeon; therefore, a wide variety of plates and screws are available to allow for rigid skeletal fixation in all areas of the craniomaxillofacial surgery.

Id.

Regardless of the plate system used, the plate must be contoured to lay passively against the underlying bone surfaces. To facilitate plate contouring, templates made of soft malleable tin alloy are available. These templates can easily be adapted to any individual bone surface merely by application of light finger pressure. The actual bone plate is then contoured on an instrument table reduplicating the individual shape of the template.

Therefore, even though the plating systems themselves are manufactured with extremely precise tolerances, a major element of imprecision remains for those surgeons who repair facial fractures and do orthognathic surgery or reconstructive procedures repositioning the facial skeletal structures to improve esthetics or function. When the osteotomy, fracture or bone graft is placed into appropriate position, the bone plate has to be manually bent to the contour of the new anatomy of the osteotomy, bone graft or fracture site. This manual manipulation creates a substantial element of imprecision even with the use of templates.

Maladapted bone plates lead to inappropriate bone contour, irritation of the overlying soft tissues, abnormal anatomy or contour defects and obviously either non-union, malunion or unaesthetic result. Importantly, after manual bending, the imprecision builds "memory" into the bone plate as the plate retains forces that would tend to inappropriately cause delayed movement of the bony segments. More precise contouring of the plate would decrease this phenomenon add lead to more accurate postoperative osseous positioning.

It would therefore be desirable to develop an apparatus and method to minimize the element of imprecision in contouring bone plates to be used in rigid fixation.

SUMMARY OF THE INVENTION

Accordingly, the present invention relates to an apparatus and method for contouring bone fixation elements such as bone plates and mesh to be used in rigid fixation of bones with substantial accuracy. The invention/instrument is preferably used as an integral part of a complete system for craniofacial surgery so that a number of plate or mesh contouring instruments currently in use are no longer necessary.

More specifically, the present invention relates to a method of contouring bone fixation elements comprising the steps of: (a) making a molded impression of the surface of the area to which the bone fixation element is to be fixed using a molding material: (b) appropriately positioning the bone fixation element to be contoured relative to the molded impression of the molding material and (c) applying compressive force to the bone fixation element to contour the bone fixation element to the shape of the cured molded impression, thereby contouring the bone fixation element to the surface of the fixation area.

The present invention also relates to an apparatus for contouring bone fixation elements including a means for forming a substantially accurate molded impression of the surface of the fixation area, a compression member and a means for applying sufficient compressive force to the compression member to contour the bone fixation element to the molded impression of the mold forming means, thereby contouring the bone fixation element to the surface of the fixation area. Preferably, the compression member comprises a molding means formed with an opposing impression to the molded impression of the surface of the fixation area.

DETAILED DESCRIPTION OF THE PRESENTLY PREFERRED EMBODIMENTS

Figure 1:
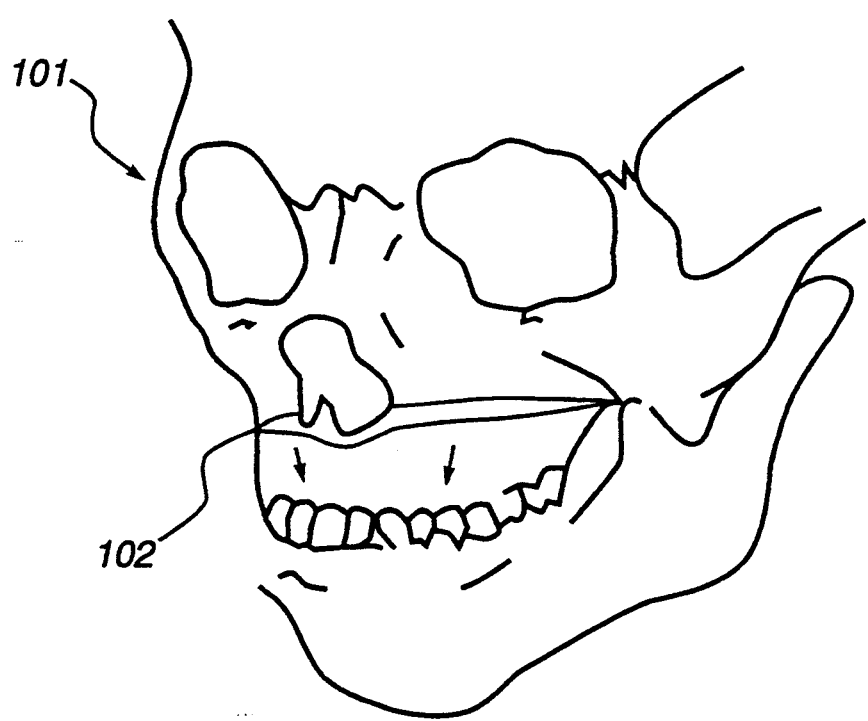
FIG. 1 is a schematic illustration of a facial skeleton showing an osteotomy of the maxilla down fractured.
Figure 2:
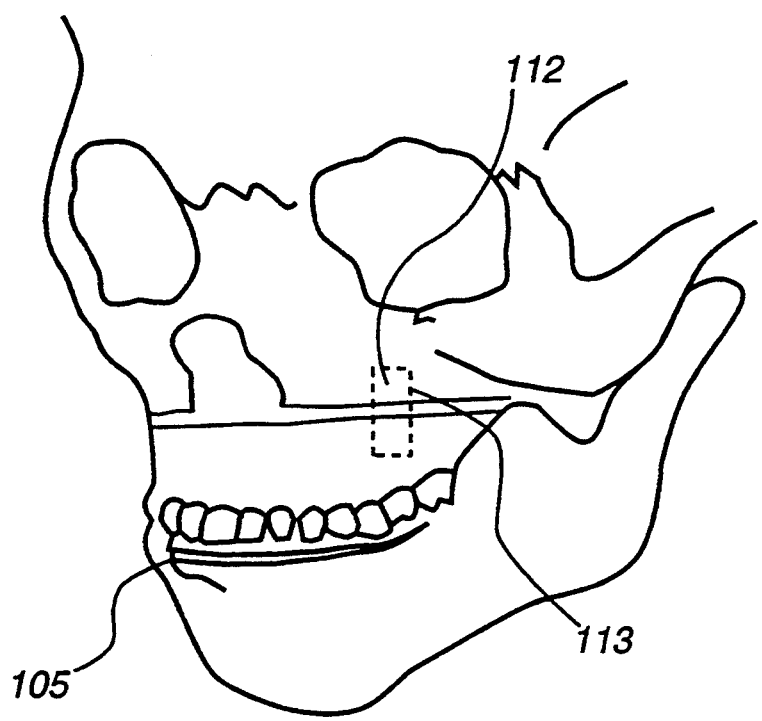
FIG. 2 is a schematic illustration of a facial skeleton showing a desired realignment of facial bones.

FIG. 1 is a schematic illustration of a facial skeleton 101 showing an osteotomy 102 of the maxilla down fractured. In FIG. 2, the facial bones have been realigned as desired using a splint index 105 to relate the upper jaw to the lower jaw. Osteotomy 102 is yet to be stabilized by a bone plate in FIG. 2. The fixation area 112 of interest is approximately defined by dashed rectangle 113.

Figure 3:
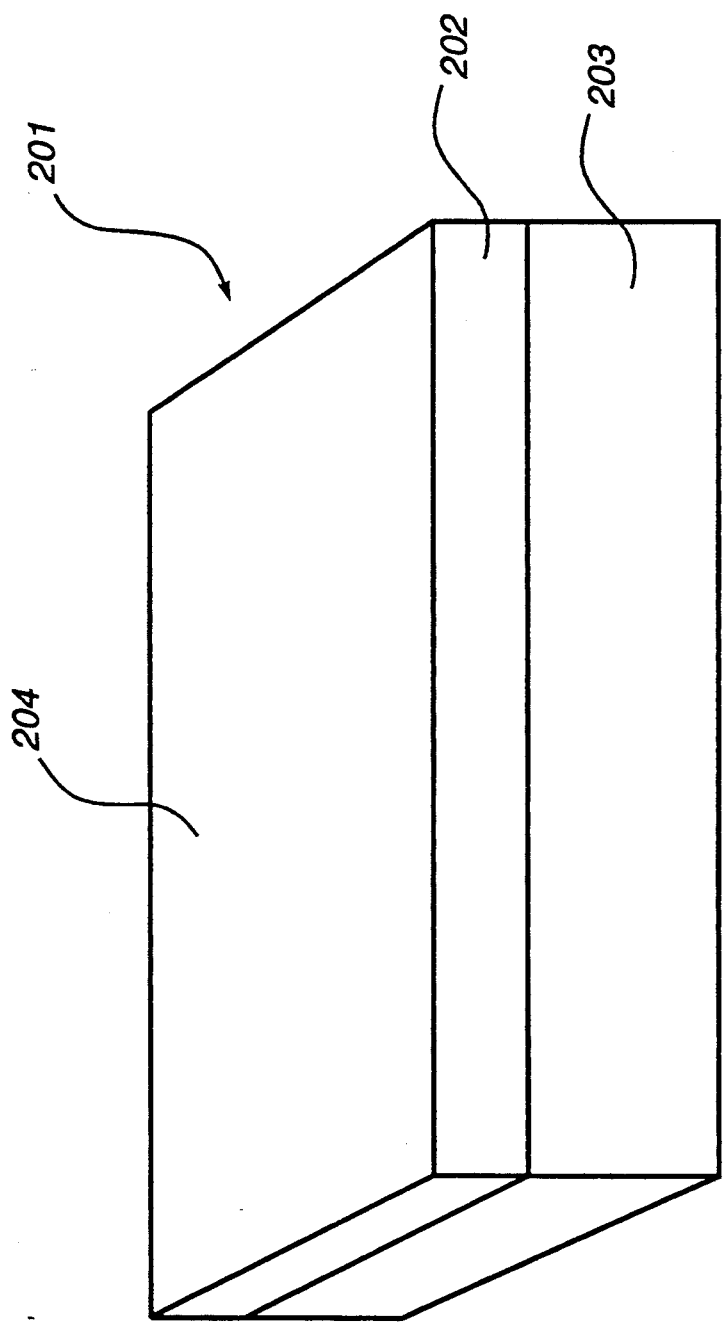
FIG. 3 is an illustration of a molding means.
Figure 4:
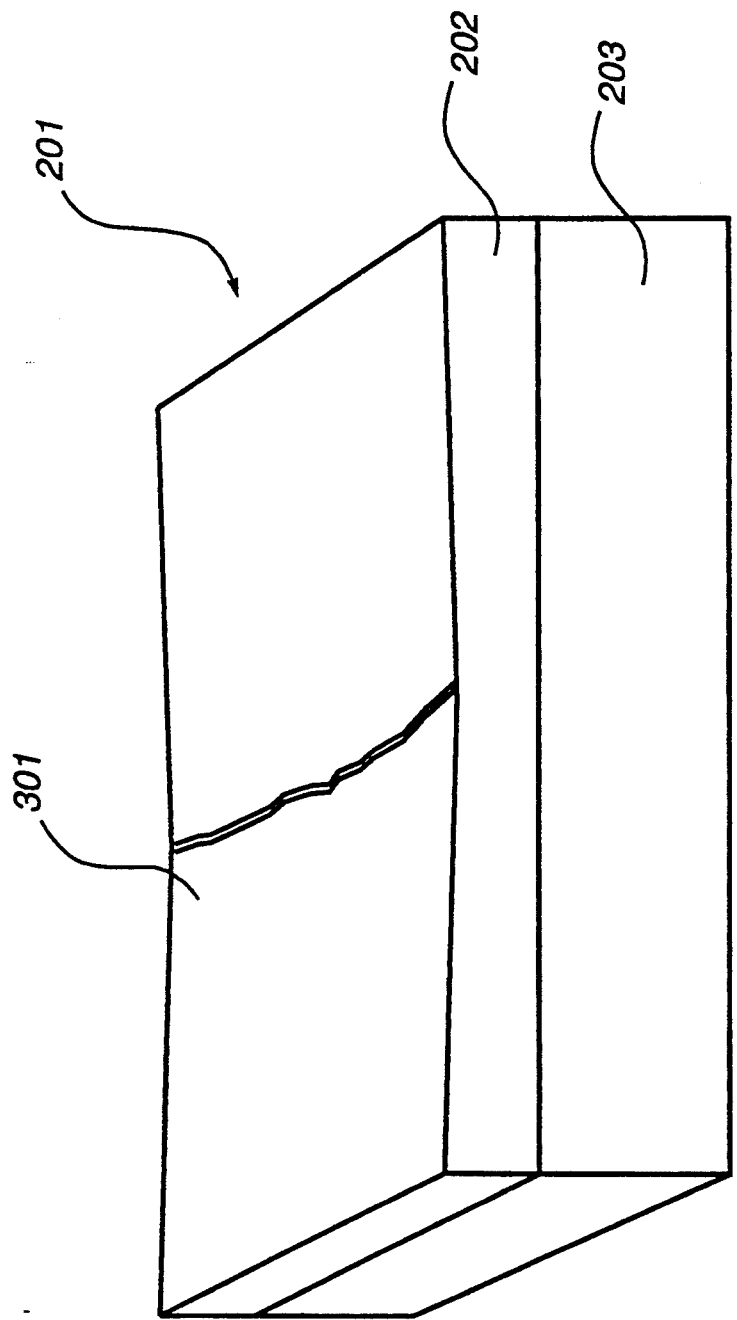
FIG. 4 is an illustration of a molding means showing a negative contoured impression therein.

In practicing the present invention, a molded impression is first made of the fixation area 112. The molding is accomplished by placing a molding means 201 (best seen in FIG. 3) comprising a molding material 202 adjacent the fixation area and applying sufficient force to create a molded impression substantially accurately representing the surface of fixation area 112. A resultant molded impression 301 is shown in FIG. 4.

When applying molding material 202 to the fixation area 112 it is preferable to first place molding material 202 in an appropriate container 203. A rigid container may be used. Container 203 must be of appropriate size and shape to enable unhindered access of molding material 202 to the fixation area 112. In FIG. 2, container 203 ends below upper surface 204 of molding material 202, thereby allowing completely unhindered access to fixation area 112. Alternatively, molding material can be placed in a flexible container comprising a material such as a flexible film. Such a flexible container will provide the freedom required to access the fixation area. A combination of rigid container and flexible film may also be used.

Molding material 202 preferably has a yield stress in the range such that molded impression 301 can be formed with a compressive force small enough that the bone positioning near osteotomy 102 (i.e., in the vicinity of fixation area 112) is not disturbed, and yet molding material 202 will maintain the impression of fixation area 112 until molding material 202 sets, hardens or cures. Molding material 202 also is preferably of sufficient structural stability upon setting such that the integrity of contoured impression 301 is maintained upon the application of force sufficient to conform a bone plate to the contour of molded impression 202 (and thereby conform the bone plate to the surface of fixation area 112).

An example of an appropriate molding material is CRANIOPLAST, which is a stoichiometric mixture of liquid monomer and methymethacrylate polymer or acrylic used primarily for cranioplasty (i.e., restructuring of skull defects). CRANIOPLAST material is generally used by neurosurgeons to recontour bony defects of the skull. It is left in place as would be an "implant." In the use of cranioplast as molding material 202, the surgeon mixes the total amount of powder and the total amount of liquid to eliminate any free monomer. The monomer is, in large quantities, toxic from a cardiovascular standpoint and is also locally irritating to tissues.

When using a molding material that may potentially have an adverse effect upon the tissue surrounding fixation area 112 or that has a surface consistency so as to stick to the bone and/or tissue in fixation area 112, it is preferable to place a film between molding material 202 and fixation area 112 to act as a protective interface prior to applying molding material 202. The film must have physical properties such that resultant impression 301 of fixation area 112 remains substantially accurate.

The film is, therefore, preferably of minimum thickness and maximum flexibility. Certain polymer films are well suited for the present use. The use of protective film is unnecessary when using CRANIOPLAST and similar compounds, which have been widely used in neuro-/craniofacial surgery without adverse postoperative reactions.

After applying molding material 202 to fixation area 112, molding material 202 is allowed to set to fix molded impression 301 of the surface of fixation area 112 within molding material 202. Depending upon the molding material used, setting may occur by a number of mechanisms including an induced chemical reaction. Preferably, setting occurs quickly to minimize the time required during the operative procedure.

Figure 5:
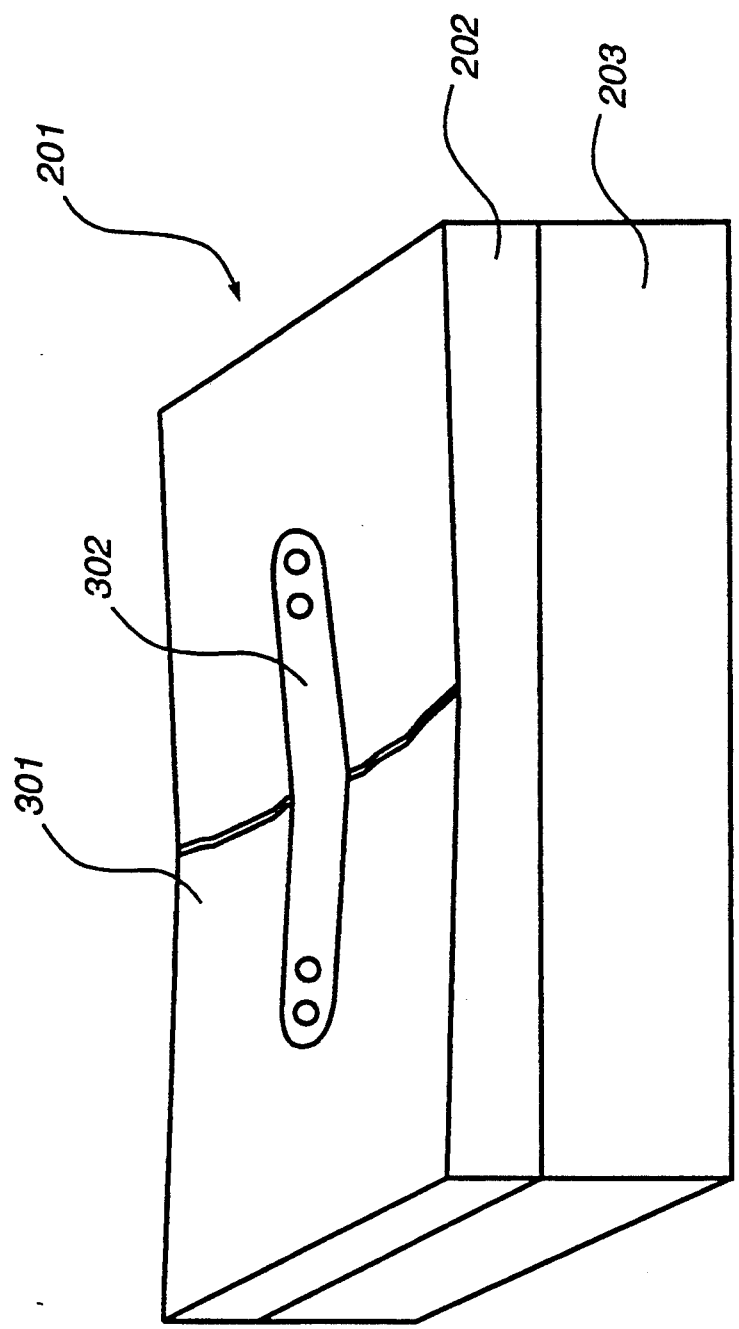
FIG. 5 is an illustration of a molding means showing a bone plate contoured to a negative impression therein.

After molding material 202 is set, bone plate or other bone fixation element 302 (whether straight, L-shaped, T-shaped, a mesh or of another initial configuration) is appropriately placed relative to contoured impression 301 (see FIG. 5) and sufficient compressive force is applied to a compression member to contour bone plate 302 to the surface of molded impression 301.

Figure 6:
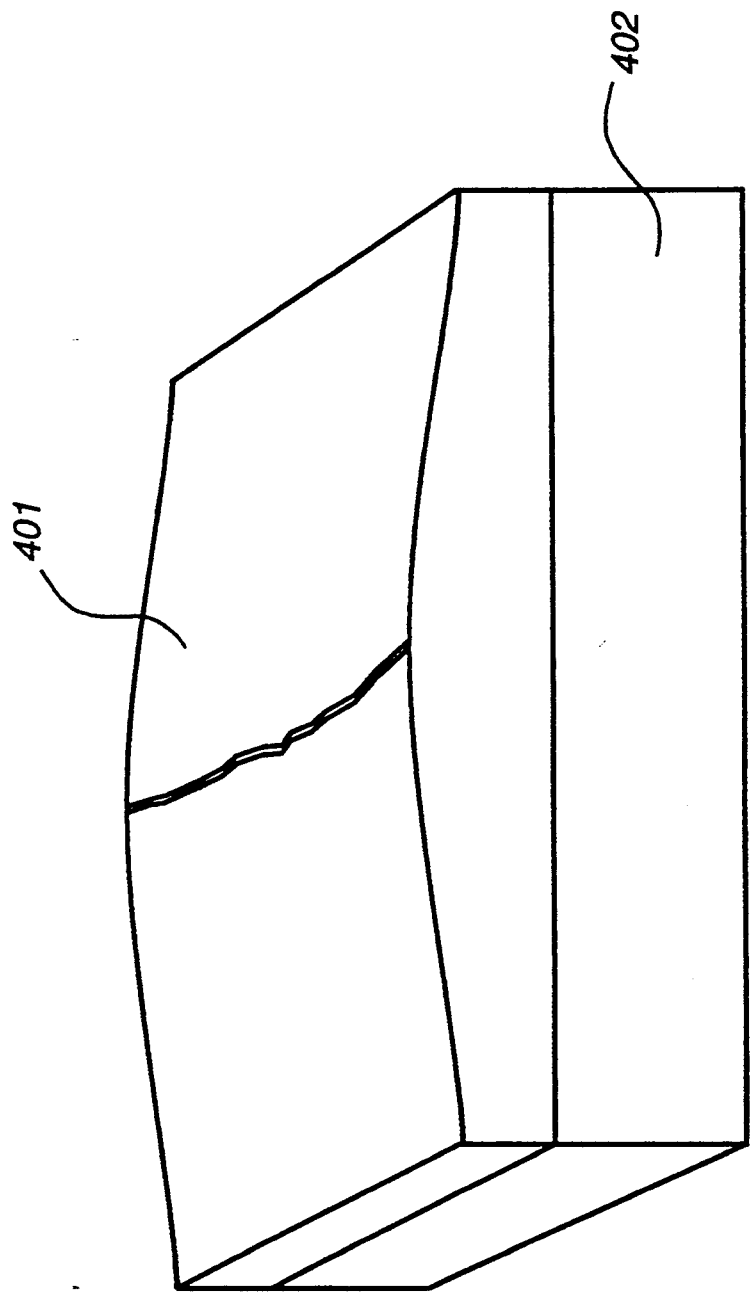
FIG. 6 is an illustration of a molding means showing a positive contoured impression therein.

In a preferred embodiment, as shown in FIG. 6, a second contoured impression is produced by forming an opposing (positive) contoured impression 401 to negative contoured impression 301 already formed. Positive contoured impression 401 is preferably formed by applying a suitable molding material to the molded impression of fixation area 112 already formed (i.e., negative contoured impression 301 illustrated in FIG. 4). An appropriate separating medium is preferably used to allow separation of the positive and negative molds. Tincture of green soap or commercial dental separating media are examples of suitable separation media. Positive contoured impression 401 is allowed to set after separation.

Upon setting of positive contoured impression 401, a bone plate or other bone fixation element is placed in a position relative to positive contoured impression 401 (or negative contoured impression 301) appropriate to contour the bone plate to the surface of fixation area 112. Negative contoured impression 301 and positive contoured impression 401 are then brought together with sufficient compressive force supplied by a compressive means to contour bone plate 302 to the surface of the fixation area 112. The compressive force can be applied by a double-action forceps 501 shown in FIG. 7.

Figure 7:
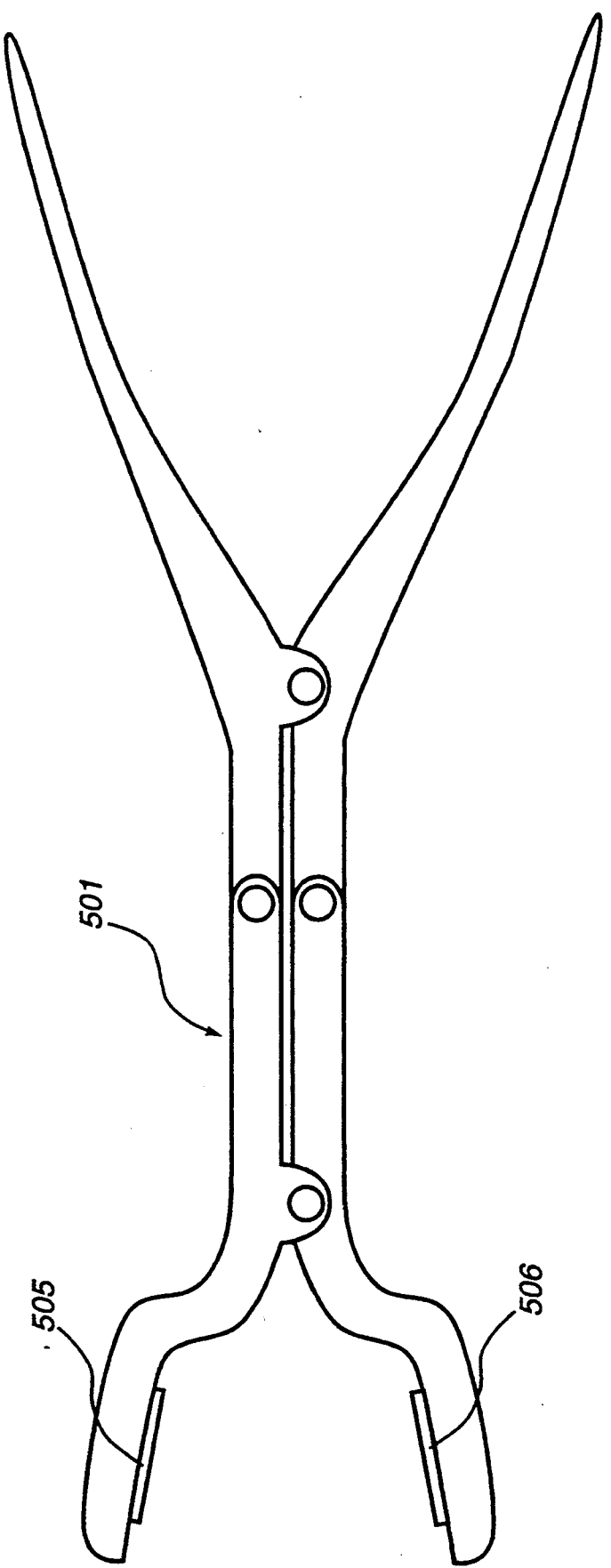
FIG. 7 is an illustration of an embodiment of a compression means.
Figure 8B:
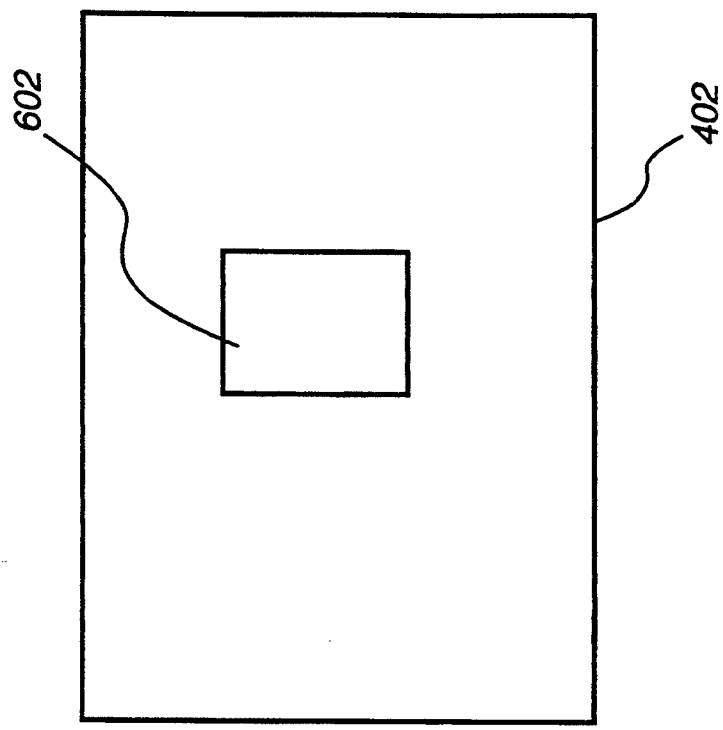
FIGS. 8A and 8B are illustrations of the underside of molding means showing attachment means disposed thereon.
Figure 8A:
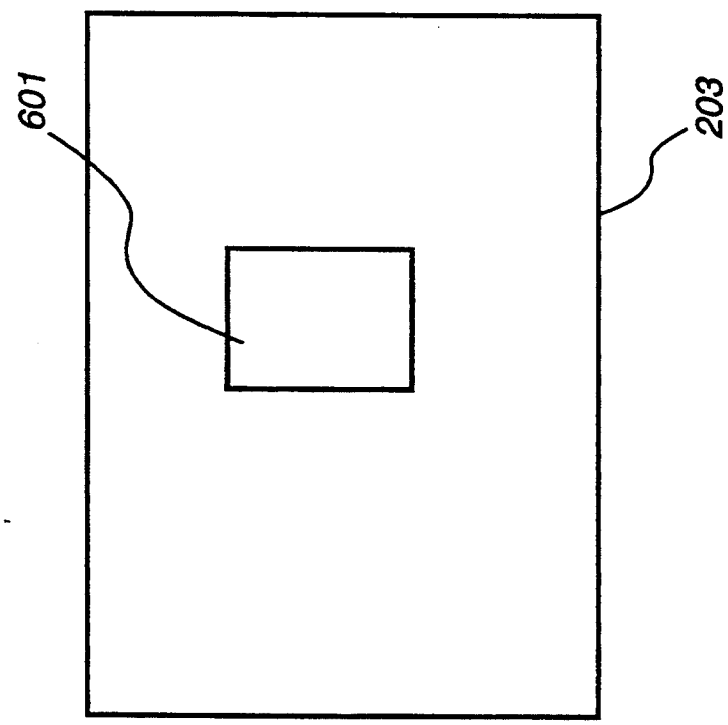
Figure 9:
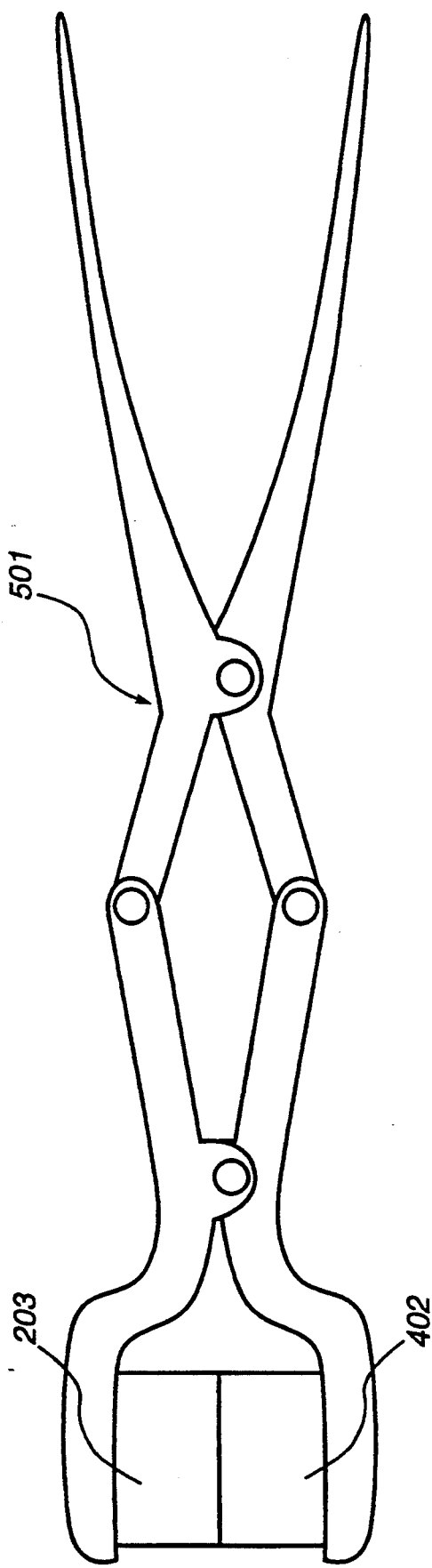
FIG. 9 is an illustration of an embodiment of a compression means with molding means attached thereto.
Figure 10:
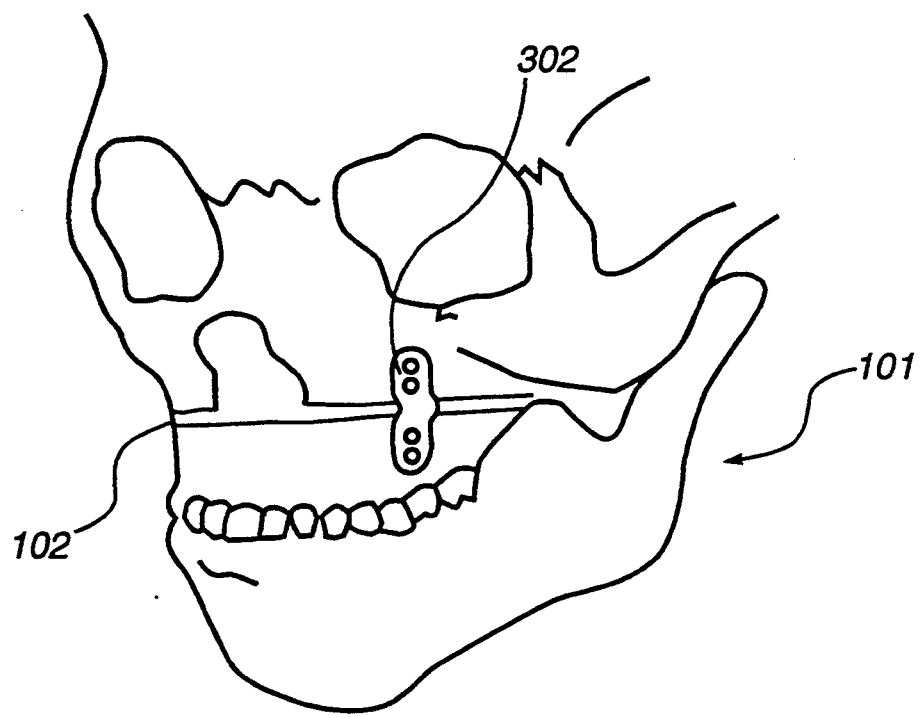
FIG. 10 is a schematic illustration of a facial skeleton showing a contoured bone plate attached thereto.

In a preferred embodiment, both container 203 of negative impression 301 and container 402 of positive compression 401 are provided with attachment means 601 and 602 respectively (See FIGS. 8A and 8B). As shown in FIG. 7, compression means 501 is preferably equipped with corresponding attachment means 505 and 506 for operative attachment containers 203 and 402. Container attachment means 601 and 602, and corresponding attachment means 505 and 506 can be of any type (e.g., a male/female bracketing system). Preferably, attachment and detachment are simple and quickly accomplished. FIG. 9 illustrates forceps 501 with containers 203 and 402 attached and in a closed position to contour a bone plate. FIG. 10 illustrates the resultant contoured bone plate fixed to fixation area 112.

In another preferred embodiment, one or more compression members comprising a semi-rigid, compressible material is/are utilized in combination with either a positive or negative mold as described above. The compressive material is preferably of appropriate compressibility such that upon application of sufficient compressive force, the bone plate is formed to the surface of the contoured impression (301 or 401). Certain hard rubbers are appropriate for use. Such compression members can preferably be in the form of plier- or forcep- like instruments having a semi-rigid, compressible material disposed upon the compressive end thereof. A variety of sizes and shapes of such compression members are preferably provided to accommodate a variety of surfaces.

Although the invention has been described in detail for purposes of illustration, it is to be understood that such detail is solely for that purpose and that variations can be made therein by those skilled in the art without departing from the spirit and scope of the invention except as it may be limited by the claims.

What is claimed is:

1. A method of immobilizing bone fragments in a fixation area by contouring with substantial accuracy a bone fixation element to a surface of said fixation area, comprising the steps of:
   a. making a molded impression of a surface of the fixation area in which the bone fragments to be immobilized are located using a molding material;
   b. appropriately positioning the bone fixation element relative to the molded impression;
   c. applying sufficient compressive force to contour the bone fixation element to the molded impression, thereby contouring the bone fixation element substantially accurately to the surface of the fixation area, and
   d. attaching and implanting the bone fixation element to the surface of the fixation area, thereby immobilizing the bone fragments in the fixation area in a desired position.

2. The method of claim 1 wherein step a comprises the steps of:
   positioning the molding material adjacent the fixation area;
   applying sufficient compressive force to the molded material to form the molded impression of the fixation area; and
   allowing the molding material to set.

3. The method of claim 2, wherein the molding material has a yield stress in an unset state in a range such that the molded impression can be formed with a compressive force small enough to prevent disturbance of the surface of the fixation area and further such that the impression is maintained until the molding material sets.

4. The method of claim 2, wherein the molding material is of sufficient structural stability upon setting to maintain the contoured impression during application of sufficient compressive force to contour the bone fixation element.

5. The method of claim 2 wherein the molding material is cranioplast.

6. The method of claim 1 wherein step c comprises the steps of:
   i. making an opposing molded impression to the molded impression made in step a; and
   ii. bringing the molded impression and the opposing molded impression together with sufficient compressive force to contour the bone fixation element therebetween substantially to the surface of the fixation area.

7. The method of claim 1 wherein the bone fixation element is selected from the group consisting of bone plates and mesh.

* * * * *